(12) United States Patent
Meakin et al.

(10) Patent No.: US 6,696,491 B2
(45) Date of Patent: Feb. 24, 2004

(54) TREATING IRRITABLE BOWEL SYNDROME OR DISEASE

(75) Inventors: Timothy David Meakin, Auckland (NZ); Dianne Cadwallader, Auckland (NZ); Craig Leonard Heatley, Auckland (NZ)

(73) Assignee: Meracol Corporation Limited, Takapuna (NZ)

( * ) Notice: Subject to any disclaimer, the term of this patent is extended or adjusted under 35 U.S.C. 154(b) by 0 days.

(21) Appl. No.: 10/275,270

(22) PCT Filed: May 11, 2001

(86) PCT No.: PCT/NZ01/00084

§ 371 (c)(1), (2), (4) Date: Mar. 27, 2003

(87) PCT Pub. No.: WO01/85162

PCT Pub. Date: Nov. 15, 2001

(65) Prior Publication Data

US 2003/0171432 A1 Sep. 11, 2003

(30) Foreign Application Priority Data

May 12, 2000 (NZ) ................................................ 504524

(51) Int. Cl.[7] .............................................. A61K 31/23
(52) U.S. Cl. ..................................................... 514/552
(58) Field of Search .......................................... 514/552

(56) References Cited

U.S. PATENT DOCUMENTS 5,496,565 A 3/1996 Heinze et al. ............... 424/502

FOREIGN PATENT DOCUMENTS

| GB | 2170407 A | 11/1999 |
| GB | 2337461 A | 11/1999 |
| WO | WO99/56733 | 11/1999 |
| WO | WO99/60167 | 11/1999 |
| WO | WO00/07627 | 2/2000 |
| WO | WO00/67728 | 11/2000 |

OTHER PUBLICATIONS from the Internet URL: http://www.hollinet.com/–jwin/Cetyl%220Myristate.htm: Amerex Corporation, "What is Cetyl Myristate—The New Amerex Pure Liquid Formula", JWInternational (Jan. 20, 1999).*

* cited by examiner

Primary Examiner—Phyllis G. Spivack
(74) Attorney, Agent, or Firm—Jacobson Holman PLLC

(57) ABSTRACT

A treatment for humans or other mammals for irritable bowel syndrome (IBS) or irritable bowel disease (IBD) is disclosed using dosage forms or compositions that comprise cetyl myristate alone or (in admixture or serially) both cetyl myristate and cetyl palmitate.

20 Claims, No Drawings

TREATING IRRITABLE BOWEL SYNDROME OR DISEASE

This is a nationalization of PCT/NZ01/00084, filed May 11, 2001 and published in English.

TECHNICAL FIELD

The present invention relates to a method of treatment and/or prophylaxis of irritable bowel syndrome (IBS) and irritable bowel disease (IBD).

BACKGROUND ART

IBS is a medical condition in which the gut functions improperly because of increased sensitivity to pain and abnormal movements. Symptoms may include abdominal discomfort or pain, often in association with urgency and diarrhea and/or constipation; bloating, spasms and painful cramping. Some hypersensitivity can be triggered by inflammation, as seen in dysentery. Colonic inflammation in can be prolonged by emotional stress.

IBD, this is also referred to as, Crohns and Colitis is a disorder involving inflammation and possible ulceration of the digestive tract. Symptoms include diarrhea, fever, anorexia, weight loss, gas, and abdominal tenderness. There may be bloody diarrhea if intestinal bleeding occurs.

It has been hypothesised that there may be an autoimmune component to both IBS and IBD where the immune system may react to the digestive cells as they break down, or food particles and bacteria that cross from the damaged intestinal walls into the blood stream. Although IBD does have similar symptoms to IBS, the cause may often be the result of an autoimmune disorder or an allergy to certain foods.

In both cases, the condition is known for inhibiting a person's social interaction and loss of dignity. Indeed some people are prevented from leaving their houses or must conduct their affairs so as to be close to a place to relieve oneself.

The present invention has surprisingly determined that the administration (particularly by ingestion) of cetyl myristate, and particularly cetyl myristate in conjunction with cetyl palmitate, provides an effective treatment of IBD and/or IBS.

Cetyl myristate and cetyl palmitate can each be sourced from animals or vegetables. Cetyl myristate is not to be mistaken for cetyl myristoleate which is a fatty acid derived traditionally from spermaceti by saponification and more recently from the tallow of bovine(s).

Reference is made to U.S. Pat. No. 4,113,881 where it is disclosed that the administration of an effective amount of cetyl myristoleate to a mammal is useful in inhibiting or relieving the symptoms of inflammatory rheumatoid, arthritis in mammals. Also in U.S. Pat. No. 5,569,676 there is disclosure of the use of cetyl myristoleate in the treatment of osteo-arthritis.

It is thought that cetyl myristate has a negligible anti-arthritic activity in laboratory experiments and reference is made to the website www.gcinutrients.com/Newletter.com. However this point is arguable and a product known as cetyl myristate sold by Amerex Corporation of 770 Sycamore Avenue, Suite J148, Vista, Calif. 92083, USA purports that cetyl myristate is useful for the treatment of arthritis.

Cetyl myristate is derived from the saturated fatty acid, myristic acid. This acid is found in nutmeg butter, in the fats of Myristicaceae, in palm seed fats, milk fats and also sperm whale oil. Reference is made to U.S. Pat. No. 2,481,365 which discloses the preparation of myristic acid from tall-oil fatty acids. It is to be noted that Amerex Corporation source cetyl myristate used in their products from sunflower oil. See their website at www.hollinet.com.

Cetyl palmitate is derived from the fatty acid, palmitic acid which occurs as the glycerol ester in many oils and fats such as palm oil or Chinese vegetable tallow. A synthetic method of preparation is to react palmitoyl chloride and cetyl alcohol in the presence of magnesium. See the Merck Index, 12th edition at page 336. Reference is also made to U.S. Pat. No. 3,169,099 which discloses a biosynthetic method of producing cetyl palmitate.

DISCLOSURE OF INVENTION

As indicated earlier the present invention is directed to the treatment and/or prophylaxis of irritable bowel syndrome (IBS) and/or irritable bowel disease (IBD) reliant upon administration (whether by self administration or otherwise) of either cetyl myristate or cetyl myristate and cetyl palmitate (whether given simultaneously in admixture or not or given serially).

The present invention also encompasses the prospect of dosage forms that in some instances might contain cetyl myristate alone and in other instances both cetyl myristate and cetyl palmitate and dosage regimes that might use one dosage form or both.

In another aspect the invention is a method of treatment and/or prophylaxis of a mammal for irritable bowel syndrome and/or for irritable bowel disease which comprises or includes administering or having self administered to such mammal an effective amount of either (a) cetyl myristate, or (b) cetyl myristate and cetyl palmitate.

Preferably said administration is orally of (b) whether as a mixture of both cetyl myristate and cetyl palmitate, or serially.

Preferably the effective amount is of (b).

Preferably said administration is with a mixture of cetyl myristate in conjunction with cetyl palmitate where the cetyl myristate comprises from 50 to 98% w/w of the mixture.

Preferably said effective amount of (a) or (b) is by means of one or more capsules.

In one type of use said mammal is a human being suffering from irritable bowel syndrome and the administration is for treatment purposes.

In another type of use said mammal is a human being suffering from irritable bowel disease and the administration is for treatment purposes.

In another aspect the invention is an oral pharmaceutical composition for treating irritable bowel syndrome which comprises or includes both cetyl myristate and cetyl palmitate.

In still another aspect the invention is an oral pharmaceutical composition for treating irritable bowel disease which comprises or includes both cetyl myristate and cetyl palmitate.

Preferably said cetyl myristate comprises at least 50% by weight of the composition.

Preferably said composition also includes at least one pharmaceutically acceptable excipient and/or diluent.

In still another aspect the invention is an oral dosage unit effective in the treatment of irritable bowel syndrome and/or irritable bowel disease, said dosage unit having either (a) cetyl myristate, or (b) a mixture of cetyl myristate and cetyl palmitate.

Preferably said dosage unit has (b) and said cetyl myristate in any such mixture comprises from 50 to 98% w/w of the mixture.

In another variant the dosage unit has (a) only and there is between 5 to 400 mg of cetyl myristate.

Preferably in the dosage use, where (b) is present, there is from 5 to 400 mg of the mixture of cetyl myristate and cetyl palmitate.

Preferably (a) or (b) is in a capsule.

Preferably said capsule also includes a pharmaceutically acceptable excipient and/or diluent.

Preferably the dosage unit includes silicon dioxide.

Preferably the dosage unit also contains calcium phosphate and/or magnesium oxide.

Preferably the dosage unit also includes additionally at one trace element.

In another aspect the invention is the use, in the manufacture of oral dosage units for the treatment or prophylaxis of irritable bowel disease in a mammal, of (a) cetyl myristate, or (b) a mixture of cetyl myristate and cetyl palmitate, or (c) cetyl palmitate.

In another aspect the invention is the use, in the manufacture of oral dosage units for the treatment or prophylaxis of irritable bowel syndrome in a mammal, of (a) cetyl myristate or (b) cetyl myristate and cetyl palmitate or, (c) cetyl palmitate.

The mixture can use cetyl myristate available from a commercial source such as EHP Products Inc., PO Box 20727, Mt Pleasant, S.C. 29465 or at Amerex Corporation, 770 Sycamore Avenue Suite J148 Vista, Calif. 92083.

The mixture can use cetyl palmitate derived from a source such as, for example, Quimica Croda, S. A. de C. V, Circuito Médicos No.47. Apdo. Postal 71-A Cd. Satélite, 53100 Naucalpan, Edo. de México, México or online at www.butterburandsage.com.

Most ideally however the mixture is synthetised from starting materials utilising the procedures as disclosed in New Zealand Patent Specification No. 332959 which involves reacting both myristic acid and palmitic acid with a cetyl alcohol at an elevated temperature in the presence of at least one acid catalyst and at least one aromatic hydrocarbon. The aromatic hydrocarbon fraction then contains the cetyl myristate and cetyl palmitate from whence it can be crystallised.

The full content of NZ 332959 is here incorporated by way of reference.

This crystallised form can then be ground up, dissolved and mixed with a suitable general pharmacy liquid to be administered to a person. The crystals are usually dissolved in hot water before adding to the pharmacy liquid which is usually a sugar syrup available from most pharmaceutical companies. The liquid is made up to a concentration of 70 w/v.

Alternatively the crystals may be ground up into a powder and combined with magnesium oxide, silicon oxide and fine di-calcium phosphate. This powder can then be transferred into capsules for oral ingestion into the body. The capsules used are VEGICAP™ that are non-gelatin containing.

The mode of administration is preferably oral. The dosage unit can be either a swallowable capsule or some alternative (preferably having the active ingredient(s) as a wax-like solid or can be an orally consumable liquid composition (eg; made up with a general pharmacy type carrier such as methyl cellulose)).

Other modes of administration can include transdermal and suppository delivery (the latter being generally contraindicated having regard to the targeted condition).

The administration process preferably involves either orally ingesting capsules or drinking the liquid formulation either on an empty stomach or not. The number of capsules or liquid taken depends on the size and severity of the persons condition.

Generally, an adult suffering from Irritable Bowel Syndrome should to take at least 4 capsules 3 times daily of a preferred dosage unit as herein described for a period of at least six to eight weeks. The doses can then be reduced to suit the individual. Whereas for a child the number of capsules taken is reduced to half or less. This dosage may be increased or decreased depending on whether the symptoms begin to clear up.

Similarly for the liquid formulation, where an amount of liquid equivalent to at least 4 capsules is prescribed which is to be taken 3 times daily. That is 4200 mg of cetyl myristate or the mixture of cetyl myristate and cetyl palmitate.

The administration process for the Irritable Bowel Disease involves initially ingesting a substantially less amount of the dosage unit effective for treating irritable bowel syndrome. It is suggested that the dose for adults and children is one 11 milligram capsule of the dosage unit as described in the invention on a daily basis for 2 or 3 weeks. The dosage rate is then increased to one 11 milligram dosage unit twice daily for 2 or 3 weeks which continues on for a further 6 to 8 weeks.

Following such a dosage rate for Irritable Bowel Disease the benefits do take time and are usually noticeable after the first three weeks of taking the said invention.

The action of the abovementioned invention can be measured through mediator relief from granulocytes and lymphocytes. Non Ig-E mediated reactions can be detected in the components of the circulating immune cells regardless of mechanism or pathway by detecting the common end point, this being a mediator release from circulating immune cells.

The use of the invention with individual diets can reduce inflammation and reactive factors of a person to a point where allergies and previous allergic reaction do not occur. This can also include reducing the reactivity to certain food intolerance.

Trials with a variety of patients reliant upon dosage forms of cetyl myristate alone have shown favorable responses insofar as relief from the symptoms of IBS and/or IBD are concerned. It has been found however that enhanced benefits occur where there is at least a small proportion of cetyl palmitate in addition to the cetyl myristate and it is to the use of one such ratio of these active ingredients that the following trial examples relate.

Examples of use follows. Each briefly describes the patient's condition before and after the stated treatment using dosage forms (ie; "of the invention") each having about 350 mg of the mixture of cetyl myristate and cetyl palmitate. That mixture comprises by weight 95% cetyl myristate and 5% cetyl palmitate by weight manufactured by the process as disclosed in NZ Patent Specification No. 332959. In addition added excipients were present in the non-gelatin two part capsule case.

TRIAL EXAMPLES

Patient 1 is Male and 72 Years of Age

Had a lower bowel operation, which had left Patient 1 with chronic diarrhea where the patient suffered up to 12 bowel motions daily.

He was assessed by a gastroenterologist in 1989 and placed on long-term use of Imodium. This was given to reduce the number of bowel motions. It was found that there were some benefits from this but he did not improve sufficiently.

He also tried Colestid and was told to remain on this indefinitely to reduce his diarrhea. This also failed to have an effect.

At the first appointment, patient 1 was provided with capsules of a dosage unit in the form of a capsule having a mixture of substantially equimolar amounts of cetyl myristate and cetyl palmitate which were taken in groupings of 4 capsules 3 times a day.

After seven weeks the bowel motions had been reduced to approximately 3 daily with an increase in the solidity of the stools being excreted.

Patient 2 is Female and 46 Years of Age.

Patient 2 developed severe diarrhea symptoms after being on a long course of medication for acne and had up to 10 bowel motions in any one day. The symptoms of diarrhea came on with some urgency and the increase in frequency became more of a problem, this was so even after receiving conventional care. This conventional care included patient 2 being referred to a prominent Auckland gastroenterologist who suspected and confirmed that Patient 2 suffered from Irritable Bowel Syndrome.

These symptoms eventually caused severe limitations on any social or physical activities of the patient.

At the first appointment patient 2 was provided with capsules of a dosage unit as described in this invention which were taken in groupings of 4 capsules 3 times daily. An initial improvement occurred almost immediately with a marked decrease in urgency.

After five weeks the frequency of bowel motions had decreased to the point where life for patient 2 had become "normal".

Patient 2 has continued to improve with one relapse occurring only when the patient stopped taking the capsules for four days.

Patient 2 has now after 1 year been able to reduce the intake of the capsules to 2 capsules 3 times a day and now has 2–3 soft-formed bowel motions per day with no cramps or urgency, and can eat all foods that previously brought on the worst symptoms.

Patient 3 is Male and is 70 Years of Age.

Patient 3 has endured chronic diarrhea since 1955, and has up to 10 bowel motions daily.

Patient 3 was diagnosed with Irritable Bowel Syndrome, and over the next 40 years, tried many different medicines including Colestid sachets, Imodium, Codeine, cholestyramine, and Dicap. However, none of the medicines listed were able to reduce the symptoms during the 40 years. During this time, patient 3 has been admitted four times to a hospital for acute exacerbations of diarrhea.

When the patient came for the first appointment, patient 3 was provided with capsules of a dosage unit as described in this invention which were, taken in groupings of 4 capsules 3 times a day. This has been increased to 4 capsules in the morning, 4 before dinner and 6 before bed.

Patient 3 now enjoys a good night of sleep, 2–3 soft-formed bowel motions per day with no urgency.

Patient 4 is Female and in Her Sixties.

Patient 4 has been diagnosed with irritable Bowel Syndrome for over a year and suffers from an extremely swollen abdomen with constant flatulence and diarrhea. Patient 4 has taken Mucilax, bran and has made major dietary alterations, all with no effect. Further effects of Irritable Bowel Syndrome to patient 4 included exhaustion, with the patient sleeping between 12–15 hours daily.

At the first appointment patient 4 was provided with capsules of a dosage unit as described in this invention which were taken in groupings of 4 capsules 3 times a day.

Within two and a half weeks, the patients abdomen returned to normal, flatulence disappeared and the patient is no longer exhausted and has seen a major increase in energy.

Patient 5 is Female and in Her Forties.

Patient 5 has for 20 years endured diarrhea and bowel incontinence and in 1995 the patients gall bladder was removed. The effect on patient 5 of this condition she has virtually been unable to leave the house. No medication brought relief of any kind.

At the first appointment patient 5 was provided with capsules of a dosage unit as described in this invention which were taken in groupings of 4 capsules 3 times a day.

Within seven days the urgency had disappeared. The bowel motion became normal in consistency, and the usual nausea and griping constantly experienced stopped within the same seven day period.

Patient 5 has maintained a dose of 3 capsules 3 times daily and has remained without symptoms for more than three months.

Patient 6 is Female and 63 Years of Age.

Patient 6 has suffered chronic irritable bowel syndrome, including the associated symptoms of a cramped, bloated feeling with persistent bowel motions that can be described as being of rabbit quality ie, many small bowel motions.

At the first appointment Patient 6 was provided with capsules of a dosage unit as described in this invention which were taken in groupings of 4 capsules 3 times daily.

This had since been reduced to a maintenance dose of four capsules twice daily.

Since taking this invention, the patients bowel motions have become normal, ie once to twice in the morning where also the bloating and abdominal pain has disappeared. She has been very happy on this medication since April 2000.

Patient 7 is Female and 50 Years of Age.

Patient 7 has suffered chronic irritable disease, or colitis since she was an infant. As a result she has had Prednesol enemas for a number of years on this basis. She states that she had colicky pains all the way through her life and always had some form of bowel dysfunction. She has used a number of products including Imodium, Slippery Elm and Peppermint.

Patient 7 is a principal in a school, and has many commitments relating to public speaking and meeting with people. The effect of irritable Bowel Syndrome did place strains of her occupation, especially in these types of situations.

At the first appointment Patient 7 was provided with capsules of a dosage unit as described in this invention which were taken in groupings of 4 capsules, 3 times daily. Patient 7 has remained on this dosage rate.

After one year on the dosage as described in this invention, her cramping and discomfort usually associated with irritable bowel syndrome has disappeared and her stools are now more formed with a normal bowel motion.

Patient 8 is Male and 32 Years Old.

Patient 8 has suffered Irritable Bowel Syndrome for 4 years, with numerous bowel motions. He had tried acupuncture, Chinese medicine and naturopaths with little success. He had even taken part in a 2 year experiment trying all manner of conventional medical exams.

The effect of Irritable Bowel Syndrome greatly effected his social and work life with increased anxiety.

Patient 8 began a course of taking capsules of a dosage unit as described in this invention which were taken in groupings of 4 capsules, 3 times daily. No initial results were noticed by the patient within the first two weeks of taking the capsules, however the patient has now noticed a vast improvement on the quality of his life. Where the anxiety previously experienced has now diminished as he no longer worries about having to relieve himself and is now able to travel overseas.

This patient is now a dosage rate of 2 capsules once a day.

Patient 9 is Female and in Her Late 30's.

Patient 9 three years ago suffered a tummy bug which left her with Irritable Bowel Syndrome. She tried many conventional and health products, including those prescribed by a doctor, none of which did not cure or alleviate her symptoms.

Her symptoms included bloating as the day wore on when eventually at night, she was unable to wear anything that put pressure on her stomach. She has described her condition as being similar to that of a baby experiencing colic. The effect was that it severely effected her social contact with people and her way of life.

She then started taking capsules of a dosage unit as described in this invention which were taken in groupings of 4 capsules, 3 times daily.

After 3 months of being on this dosage rate her symptoms have just about disappeared. With her bowel movements and regularity back to normal.

She has now decreased her dosage to 3 capsules 3 times a day. However, if she feels that her stomach is starting to bloat she will increase her dose for a couple of days until her stomach settles again.

Patient 10 is Female and is 30 Years of Age.

Has suffered Irritable Bowel Syndrome for 9 years and has tried all manner of natural remedies, including acidophilus, slippery elm, magnesium, aloe vera and Metamucil. She changed her diet cutting out foods that were likely to trigger a reaction.

IBS effected her social and working life, where the onset of IBS would be without notice and immediate.

She then started taking capsules of a dosage unit as described in this invention which were taken in groupings of 4 capsules 4 times a day. After one week she noticed a change and now her life is back to normal. Where the urgency and immediacy of her bowel motions have almost disappeared and she can lead a normal social and working life.

Her dosage is now down to 6 capsules a day.

Patient 11 is Male.

Patient 11 for the last 10 years had suffered bouts of diarrhea and bloating several times each month. These bouts would happen at any time and without warning and involved between 3 to 6 bowel motions. Patient 11 has had bowel cancer and has subsequently lost a large part of his lower bowel.

He has tried various conventional medications as suggested by his doctor, health shops and friends over the years trying to overcome this problem and nothing seemed to work.

He then started taking capsules of a dosage unit as described in this invention which were taken in groupings of 4 capsules 3 times a day.

Having taken the capsules for nearly 3 months diarrhea has only occurred once.

The effect is that the patient 11 is feeling a lot fitter, healthier and no longer worries about the immediacy of or urgency with which the symptoms of IBS.

What is claimed is:

1. A method of treatment and/or prophylaxis of a mammal for irritable bowel syndrome and/or for irritable bowel disease which comprises administering or self administering to such mammal in need there of an effective amount of either
   (a) cetyl myristate, or
   (b) cetyl myristate and cetyl palmitate.
2. The method as claimed in claim 1 wherein said administration is orally of (b) whether as a mixture of both cetyl myristate and cetyl palmitate, or serially.
3. The method of claim 1 where the effective amount is of (b).
4. The method as claimed in claim 1 wherein said administration is with a mixture of cetyl myristate in conjunction with cetyl palmitate where the cetyl myristate comprises from 50 to 98% w/w of the mixture.
5. The method of claim 1 wherein said effective amount of (a) or (b) is by means of one or more capsules.
6. The method of claim 1 where said mammal is a human being suffering from irritable bowel syndrome and the administration is for treatment purposes.
7. The method of claim 1 wherein said mammal is a human being suffering from irritable bowel disease and the administration is for treatment purposes.
8. The method of claim 1 where both cetyl myristate and cetyl palmitate in admixture are administered, the ratio by weight to weight being 95:5 respectively.
9. A method of treatment of a human being for irritable bowel syndrome which comprises administering to that human an effective amount of cetyl myristate.
10. A method treatment of a human being for irritable bowel disease which comprises administering to that human an effective amount of cetyl myristate.
11. An oral pharmaceutical composition for treating irritable bowel syndrome and/or irritable bowel disease which comprises both cetyl myristate and cetyl palmitate.
12. The composition of claim 11 wherein said cetyl myristate comprises at least 50% by weight of the composition.
13. The composition of claim 11 which further comprises at least one pharmaceutically acceptable excipient and/or diluent.
14. An oral dosage unit effective in the treatment of irritable bowel syndrome and/or irritable bowel disease, said dosage unit comprising
   a mixture of cetyl myristate and cetyl palmitate.
15. The dosage unit as claimed in claim 14 wherein said cetyl myristate comprises from 50 to 98% w/w of the mixture.
16. The dosage unit of claim 14 wherein said dosage unit is a capsule.
17. The dosage unit as claimed in claim 16 wherein said capsule further comprises pharmaceutically acceptable excipient and/or diluent.
18. The dosage unit of claim 17 which comprises silicon dioxide.
19. The dosage unit of claim 14 which also contains calcium phosphate and/or magnesium oxide.
20. The dosage unit of claim 14 which further comprises at least one trace element.

* * * * *